United States Patent [19]

Eberbach

[11] Patent Number: 5,116,357
[45] Date of Patent: May 26, 1992

[54] HERNIA PLUG AND INTRODUCER APPARATUS

[76] Inventor: Mark A. Eberbach, 4232 Winding Willow Dr., Tampa, Fla. 33624

[21] Appl. No.: 667,456

[22] Filed: Mar. 11, 1991

Related U.S. Application Data

[63] Continuation-in-part of Ser. No. 595,956, Oct. 11, 1990.

[51] Int. Cl.⁵ ............................ A61F 13/00; A61F 15/00
[52] U.S. Cl. ........................................ 606/213; 606/151; 606/1; 623/11; 602/76
[58] Field of Search ................... 606/1, 110, 113, 114, 606/127, 151, 200, 213; 604/11, 13, 15; 623/11, 12; 128/155, 156, 168, 887, 830, 837, 849, 850, 851, 854

[56] References Cited

U.S. PATENT DOCUMENTS

| | | | |
|---|---|---|---|
| 3,102,541 | 9/1963 | Adams | 604/15 |
| 3,814,095 | 6/1974 | Lubens | 128/156 |
| 3,874,388 | 4/1975 | King et al. | 623/11 |
| 4,007,743 | 2/1977 | Blake | 623/11 |
| 4,347,847 | 9/1982 | Usher | 606/151 |
| 4,610,659 | 9/1986 | Friese | 604/11 |
| 4,744,364 | 5/1988 | Kensey | 606/213 |
| 4,769,038 | 9/1988 | Bendavid | 606/151 |
| 4,821,741 | 4/1989 | Mohajer | 128/837 |
| 4,854,316 | 8/1989 | Davis | 623/12 |
| 4,981,465 | 1/1991 | Ballan et al. | 128/887 |

Primary Examiner—Stephen C. Pellegrino
Assistant Examiner—Glenn K. Dawson
Attorney, Agent, or Firm—Dominik, Stein, Saccocio, Reese, Colitz & Van Der Wall

[57] ABSTRACT

An apparatus for the repair of hernias comprising a plug positionable in an opening in the abdominal wall; a patch positionable over weakened portions of the abdominal part adjacent to the opening, a central extent of the patch being coupled to the proximal end of the plug; and a resilient means coupled to the patch and provided with memory to assume a configuration of an extended shape for the proper positioning of the patch with respect to the weakened portions of the abdominal part.

13 Claims, 8 Drawing Sheets

HERNIA PLUG AND INTRODUCER APPARATUS

RELATED APPLICATION

This application is a continuation in part application of copending U.S. patent application Ser. No. 07/595,956 filed Oct. 11, 1990.

BACKGROUND OF THE INVENTION

1. Summary of the Invention

This invention relates to medical apparatus and, more particularly, to the repair of hernias with a laparoscopic approach and associated plugs and patches.

2. Summary of the Background Art

A hernia is one of the most common ailments of mankind. Approximately five percent of the adult male population is affected. Basically, a hernia is a weakness or hole in the abdominal wall through which abdominal contents such as bowels may protrude. Inguinal or groin hernias normally occur at one or more of three locations. The first location is in the weakened wall or inguinal floor of the abdomen in Hesselbach's triangle. This type of hernia is called a direct hernia. An indirect hernia occurs at the internal ring adjacent to the vas deferens as it exits the abdomen to become part of the spermatic cord. The third is a femoral hernia that occurs adjacent and medial to the femoral blood vessels.

All hernias represent a potentially life threatening condition and once diagnosed they should be repaired unless there is some contraindication.

The surgical repair of an inguinal hernia (inguinal herniorrhaphy) is a common procedure which surgeons often perform on an outpatient basis. It is estimated that 500,000 are performed each year in the United States. According to the procedure, an anesthetic is first administered to the patient and the surgeon then makes a large incision, about 6 inches, in the patient just above the inguinal ligament. Supporting abdominal muscles and fascia are dissected to reveal the hernia sac. The herniated contents protruding through the opening in the abdominal wall are returned to the abdomen. Thereafter, the surgeon closes the hernia sac. The local tissues are then sutured together from opposite sides of the weakened tissue, hole or hernia. The stretched or otherwise weakened tissue may be cut away. Where appropriate, a patch of artificial material may be sutured to the normal tissue to replace the stretched or otherwise weakened tissue or to reenforce over the outside of the repair. The incision is then closed over the repair. Recovery time necessary prior to heavy lifting or strenuous labor is usually six to eight weeks and recurrence rates may approach twenty percent.

Another more difficult approach which is less common, but more physiological, is to make an incision in the abdomen superior or cephalad to the hernia. The surgeon cuts through the abdominal wall to the last layer (the peritoneum). Dissection continues in this preperitoneal approach and exposes the hernia defect from the inside. Again direct suture repair or patch repair may be performed. The recurrence rates are low with an inside patch repair because increased intra-abdominal pressure only serves to force the patch more firmly into place to plug the hole similar to a drain plug in a bathtub.

Although common, the standard operational procedures for repair of a hernia is undesirably lengthy and, consequently, costly, requires a large incision with the excessive dissection of normal tissue, causes excessive pain and discomfort to the patient, involves unacceptably long recovery and work disability time, and results in an unacceptably high recurrence rate.

Accordingly, it is an object of the present invention to provide an apparatus for the repair of hernias comprising a plug positionable in an opening in the abdominal wall; a patch positionable over weakened portions of the abdominal part adjacent to the opening, a central extent of the patch being coupled to the proximal end of the plug; and a resilient means coupled to the patch and provided with memory to assume a configuration of an extended shape for the proper positioning of the patch with respect to the weakened portions of the abdominal part.

It is a further object of the present invention to employ laparoscopic techniques for the repair of hernias thereby reducing the length of the incision along with the unnecessary dissection of normal tissue.

It is a further object of the present invention to utilize a new laparoscopic approach via the preperitoneal space.

It is a further object of the present invention to minimize the time and cost of hernia operations.

It is a further object of the present invention to minimize a patient's pain and discomfort associated with a hernia operation.

It is a further object of the present invention to shorten the recovery time normally attendant with a hernia operation.

It is a further object of the present invention to reduce or preclude the recurrence of hernias.

Lastly, it is an object of the present invention to utilize a plug/patch assembly for the repair of a hernia wherein the patch has its own memory for assuming its proper orientation over the area to be repaired.

Further objects of the present invention are to internally plug and or patch and restore stretched or weakened areas of an abdominal wall or overt hernia defects and to simultaneously patch all primary and secondary abdominal areas which are predisposed to hernias.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with specific embodiments shown on the attached drawings. For the purpose of summarizing this invention, the invention may be incorporated into an improved apparatus for the repair of hernias comprising a plug positionable in an opening in the abdominal wall; a patch positionable over weakened portions of the abdominal part adjacent to the opening, a central extent of the patch being coupled to the proximal end of the plug thus constituting a flange; and a resilient means coupled to the flange and provided with memory to assume a configuration of an extended shape for the proper positioning of the flange with respect to the weakened portions of the abdominal part.

The resilient means is a washer-shaped member secured to the flange adjacent to its periphery. The washer-shaped member is between about 4.0 and 6.0 centimeters in its exterior diameter and is deformable to a configuration for positioning within a sleeve. The resilient means may be a serpentine-shaped member. The resilient means may be a plurality of L-shaped components, each component having one leg positioned within the plug and parallel to the axis of the plug and having another leg coupled with respect to the flange and extending radially from the axis of the plug wherein the plurality of L-shaped components are bendable to an essentially linear configuration for positioning within a sleeve.

The invention may also be incorporated into apparatus wherein the plug is fabricated of fabric rolled spirally into a cylindrical configuration. In the alternative, the plug may be of a one piece construction. The resilient members are fabricated as proximally extending members from the plug. The exterior surface of the plug may be roughened to increase its coefficient of friction. The exterior surface of the plug may include frictional members extending radially from the exterior surface of the plug. The apparatus further includes a sheath for the receipt of the plug/flange assembly, the sheath being flexible.

The invention may also be incorporated into a laparoscopic introducer for a plug/flange assembly comprising a cylindrical sleeve of a length to extend from exterior of a patient, through a laparoscopic opening into a surgical cavity; and a plunger having a cylindrical exterior configuration positioned within the sleeve, the plunger having a distal end of a reduced radial size to form a space at the distal end of the sleeve for the receipt of patch material of a plug/flange assembly.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Overview

Figure 1:
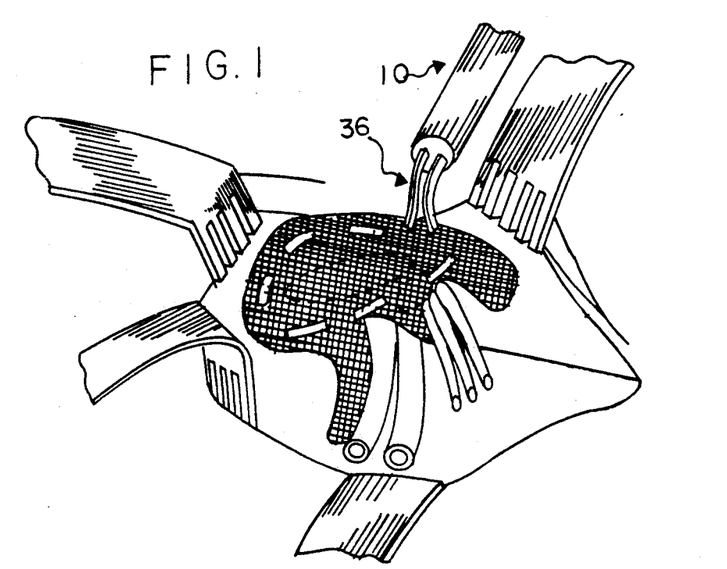
FIG. 1 shows a portion of the abdominal wall from the inside where hernias normally occur and also illustrating therein a patch for their repair and the precluding of further hernias.

Shown in FIG. 1 is that portion of the abdomen where hernias normally occur. Whether through old age, accident, personal abuse, congenital problems, or the like, the inguinal floor of the abdomen known as Hesselbach's triangle may become weakened to the point whereby inner abdominal contents such as a bowel may protrude. When the organ extending therethrough is a portion of the bowel, serious illness or even death may occur. This is a direct inguinal hernia. There are two other common types of groin hernias. These occur adjacent to either the vas deferens (indirect) or the femoral vessels (femoral hernia). When either the internal inguinal ring through which the vas deferens passes or the abdominal wall adjacent to the femoral vessels becomes enlarged, an opening is created through which abdominal contents such as intestines may protrude thereby constituting a hernia. In the past, surgeons operated upon the hernia area either from above (preperitoneal) or below (anterior) with large incisions which lead to great disability.

The present invention includes introducers 10 with plugs 12 and patches 14, with the patches designed to cover all three areas where groin hernias normally occur and accomplishes a more physiological repair with a smaller incision utilizing laparoscopic technique by use of a specifically designed introducer and patch and a preperitoneal approach presently not used.

Patch and Introducer

The patch 14 is preferably fabricated of a mono-filament thread which is woven, knitted or otherwise formed into a fabric which is then cut to a shape. It has a main central portion 16 to cover the inguinal floor area where direct groin hernias normally occur. The shape is generally in the shape of a trapezoid with a major axis and a minor axis.

Extending outwardly from one edge are three asymmetrical portions, formed as three fingers 18, 20 and 22 with the central finger being smaller than the other two. Formed between the fingers are spaced concave recesses, sized and positioned to be placed in close proximity to the vas deferens and or the femoral vessels. Those portions of the patch located adjacent to the recesses are thus adapted to cover those areas of the abdomen where indirect and femoral hernias normally occur. At the same time, the central portion of the patch is adapted to cover the area of the inguinal floor where direct hernias normally occur.

The thread from which the patch is fabricated are of a surgically clean material which is durable, flexible, essentially inextensible and resistant to corrosion from bodily fluids. By way of example, one acceptable material is polypropylene such as Marlex ® mesh. Marlex is a trademark of Johnson & Johnson Company of Sommerville, N.J. Further, by way of example, one acceptable material thread is Nylon ® polymer. Nylon is a registered trademark of the E. I. DuPont DeNemours Company of Wilmington, Del.

Formed into the patch is a passageway 30 for receiving a loop 32, the loop constituting the distal part of the patch delivery assembly or introducer 10. The passageway is shown in the preferred embodiment as spaced axial slits 34 through which the loop is threaded. The passageway may take other forms such as an elongated extent of fabric, preferably of the same material as the patch, secured in a symmetrical manner interior of the periphery of the patch.

When distended, the loop 32 is in the form of an ellipse which has a major axis and a minor axis coextensive with the major axis and minor axis of the patch. In the alternative, the loop and its passageway may take one of many other forms such as that of a teardrop, circle or oval as shown in FIGS. 1, 2, 4, 5, 6, 12, 13 and 14. Other smoothly shaped, curved configurations could be utilized. The periphery of the patch is at varying distances from the passageway and loop. Hence the peripheral portions of the patch do not immediately reach all the areas of direct as well as indirect hernias. Consequently, conventional laparoscopic techniques must be employed by the surgeon to provide final positioning of the parch after initial placement by the loop.

Figures 2, 3, 4:
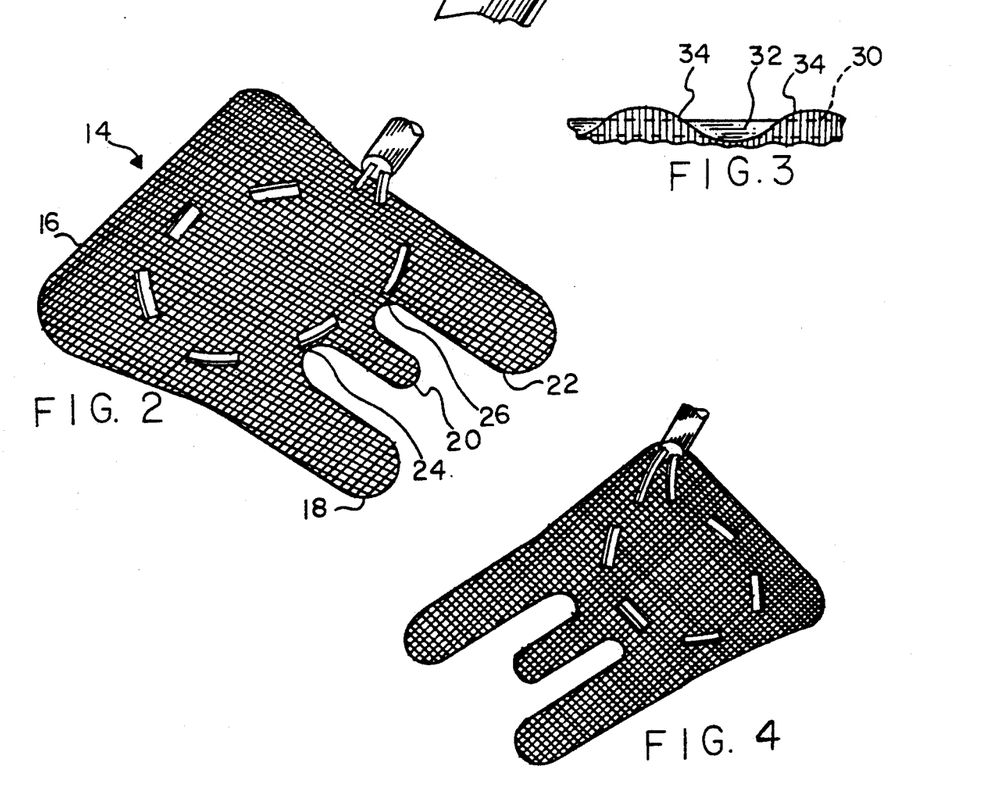
FIG. 2 is a perspective view of the patch constructed in accordance with the principles of the present invention and as shown in FIG. 1, shown in association with the patch is an introducer functioning as a delivery assembly for the patch.
FIG. 3 is a sectional view of a portion of the patch shown in FIG. 2.
FIG. 4 is a perspective view of a patch similar to that of FIG. 2, but in mirror image for use on the other side of the patient and illustrating a smaller design as for a child.

Located within the passageway is the loop 32 of the ribbon 36, constructed of surgically antiseptic material and shaped in a smoothly curved configuration such as an ellipse when expanded. The loop 32 is of a size and configuration to be received within the passageway of the patch 14. The loop is at the far or distal end of the plunger 42. As shown in FIG. 2, the loop of the ribbon holds the majority of the patch in an extended orientation for initial placement on the abdominal wall over the hernia to be repaired. The proximal end of the loop is a ribbon extension of the loop which, like the loop, is flexible, but sufficiently rigid to function is association with the plunger 42 so that a surgeon may remotely push, pull, or rotate the loop and, consequently, the patch, during an operation. The plunger 42 includes a cylinder 44 and guide beam 46. The introducer 10 includes the plunger 42 and sheath 48.

The patch 14 as well as its supporting ribbon loop 32 and its distal extensions 52 are preferably prepackaged in a delivery assembly, the introducer 10, prior to use by insertion through a sleeve which is conventionally placed in a patient by a trochar.

Figures 7, 8, 9, 10, 15, 16:
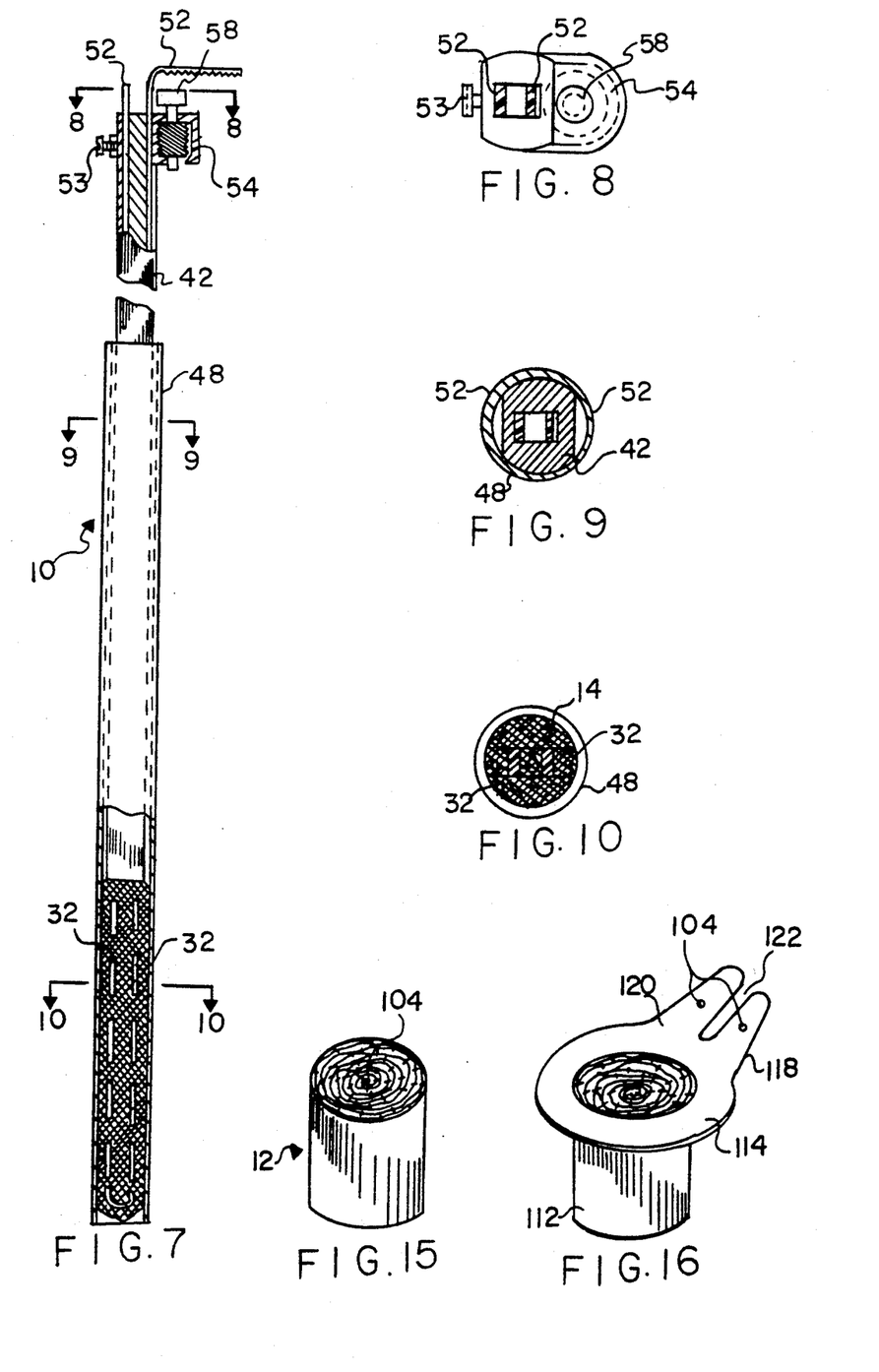
FIG. 7 is an elevational view, partly in section, of the introducer of FIGS. 2 through 6 but with the patch prior to discharge.
FIGS. 8 through 10 are sectional views of the introducer of FIG. 7 taken along lines 8—8, 9—9 and 10—10 of FIG. 7.
FIGS. 15 and 16 illustrate a plug useable independently of, or in association with, the apparatus shown in FIGS. 1 through 14.

The delivery assembly 10 is best seen in FIG. 7. Its major components include an external cylindrical sheath 48 and an internal plunger 42. The proximal end of the plunger includes a set screw 52 oriented to releasable secure one end of the ribbon. The proximal end of the plunger/expander assembly 42 includes a worm gear 54 for coupling with teeth formed on the ribbon. Note FIG. 8. The worm gear 54 is a preferred mechanism since it permits precise adjustments in the moving of the loop and patch. In this manner, the surgeon may effect the precise movement of the loop in either direction but prevents the inadvertent movement therof. A cylindrical guide beam 46 with flat faces is located interiorly along the length of the introducer 10 to act as a bearing surface during operation of the set screw 52 and worm gear 54 and for guiding the movement of the ribbon 36 with respect to the plunger 42 during the blooming of the patch. A weld 56, a dot of glue, or the like couples the proximal end of the patch to the distal end of the plunger.

Figures 11, 12, 13, 17, 18, 19:
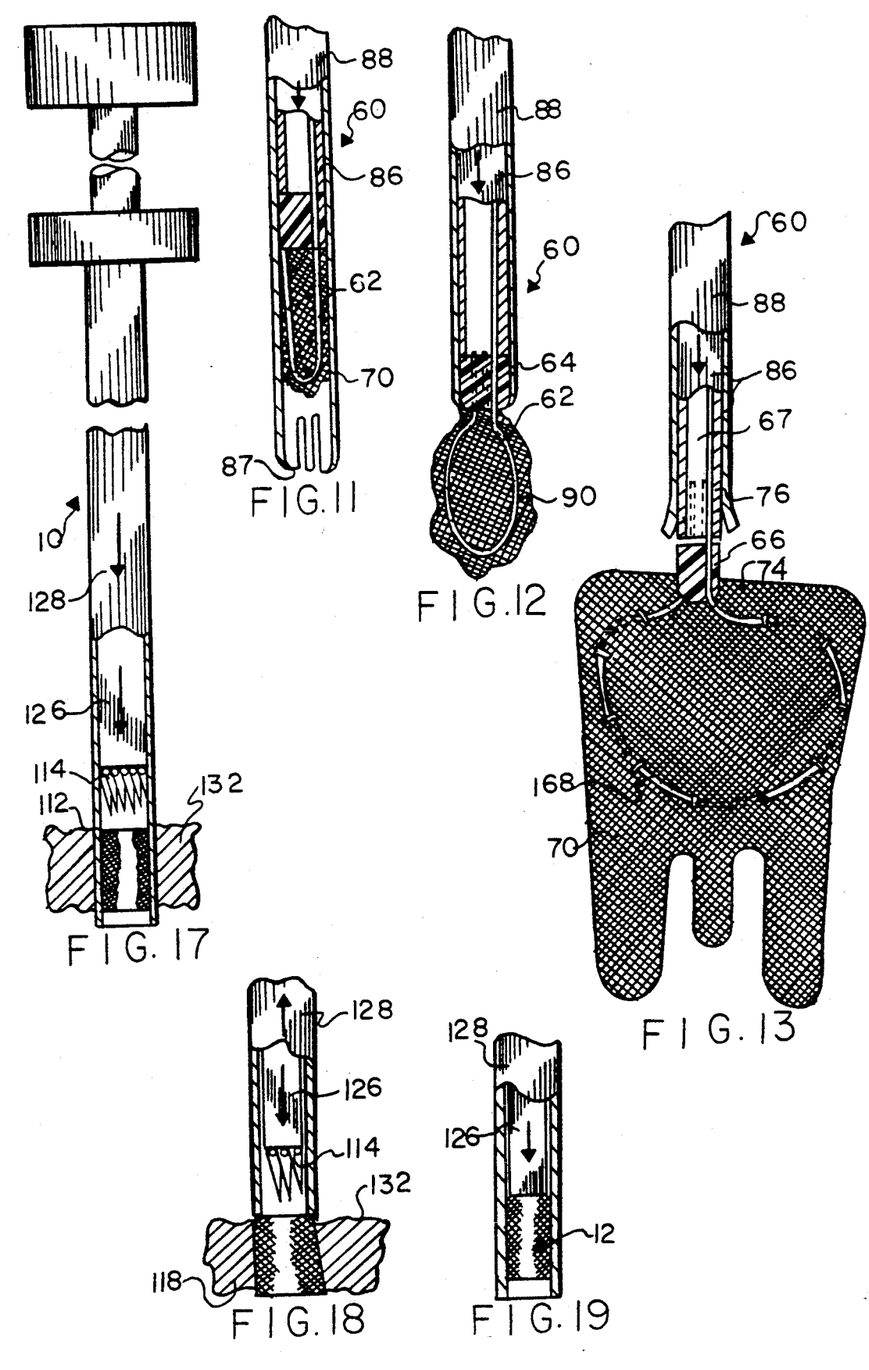
FIGS. 11 through 13 are elevational views, partly in section, of an alternate embodiment of an introducer for the patch.
FIGS. 17 through 19 are elevational views, partly in section, of an introducer for the plug constructed in accordance with yet a further embodiment of the invention.

In operation and use, the introducer 10 is inserted through the sleeve with its distal end adjacent to the area of the abdominal wall to be patched. The plunger/expander 42 and patch 14 are pre-positioned within the sheath 48 as shown in FIG. 7. The introducer 10 then is moved forward by the surgeon moving the introducer with respect to the sleeve or withdrawing the sleeve with respect to the introducer. The ribbon, loop and patch move with the introducer when relative movement occurs between the sleeve and introducer. The plunger is depressed to dispense the main body of the patch. Thereafter, the surgeon rotates the knob 58 of the worm gear to enlarge the loop and cause the patch to bloom into the anatomically desired orientation as shown in FIGS. 1, 2 and 13. Using a second laparoscopic opening, the surgeon will position the edges of the patch into final position. The patch will remain in position due to the pressure applied to it by the normal abdominal contents. Staples or sutures could be employed to further secure the patch in its final position.

Alternate Embodiment.

The FIG. 11 through 13 embodiment illustrates an alternate introducer for holding the patch and for pushing it outwardly from the distal end of the sleeve. In this embodiment, the ribbon 62 is formed with an enlargement or block 64 at its distal end. The block has a slot 66 through which the ribbon passes to form a loop 68, in a manner similar to a lasso, which supports a patch 70 as in the prior embodiment. The slot is preferably formed with a ratchet tooth to sequentially engage ratchet teeth on the ribbon to allow for only one way movement of the ribbon during blooming of the patch.

The proximal end of the block is not coupled to the distal end of the plunger. Further, the proximal end of the patch is coupled to the distal end of the block as by a weld 74 to hold the proximal end of the patch in position as the distal end of the ribbon is moved distally to effect the blooming of the patch. The guide beam 76 has one flat side to receive and guide the ribbon 62 for movement with respect to the plunger cylinder 78 during the blooming of the patch 70.

In this embodiment, the distal end of the sheath 88 has axially slits 82 at a plurality of locations with the end forming a slight taper or bend. In this manner, the plunger 86 may be moved with respect to the sheath 88, from FIG. 11 position to the FIG. 12 position. The surgeon can feel the slight resistance caused by the block 64 against the bend indicating that the FIG. 12 position has been reached. Thereafter, the proximal end of the ribbon may be fed distally with respect to the plunger and block to effect the blooming of the patch. Thereafter, the block is moved distally a greater distance until the FIG. 13 position is reached and the resistance to movement is no longer felt by the surgeon, thus freeing the patch from the introducer. The patch 70, loop 68 and block 64 are then cut free of the plunger 86 and the remainder of the ribbon.

Further Alternate Embodiment

Figures 5, 6, 14:
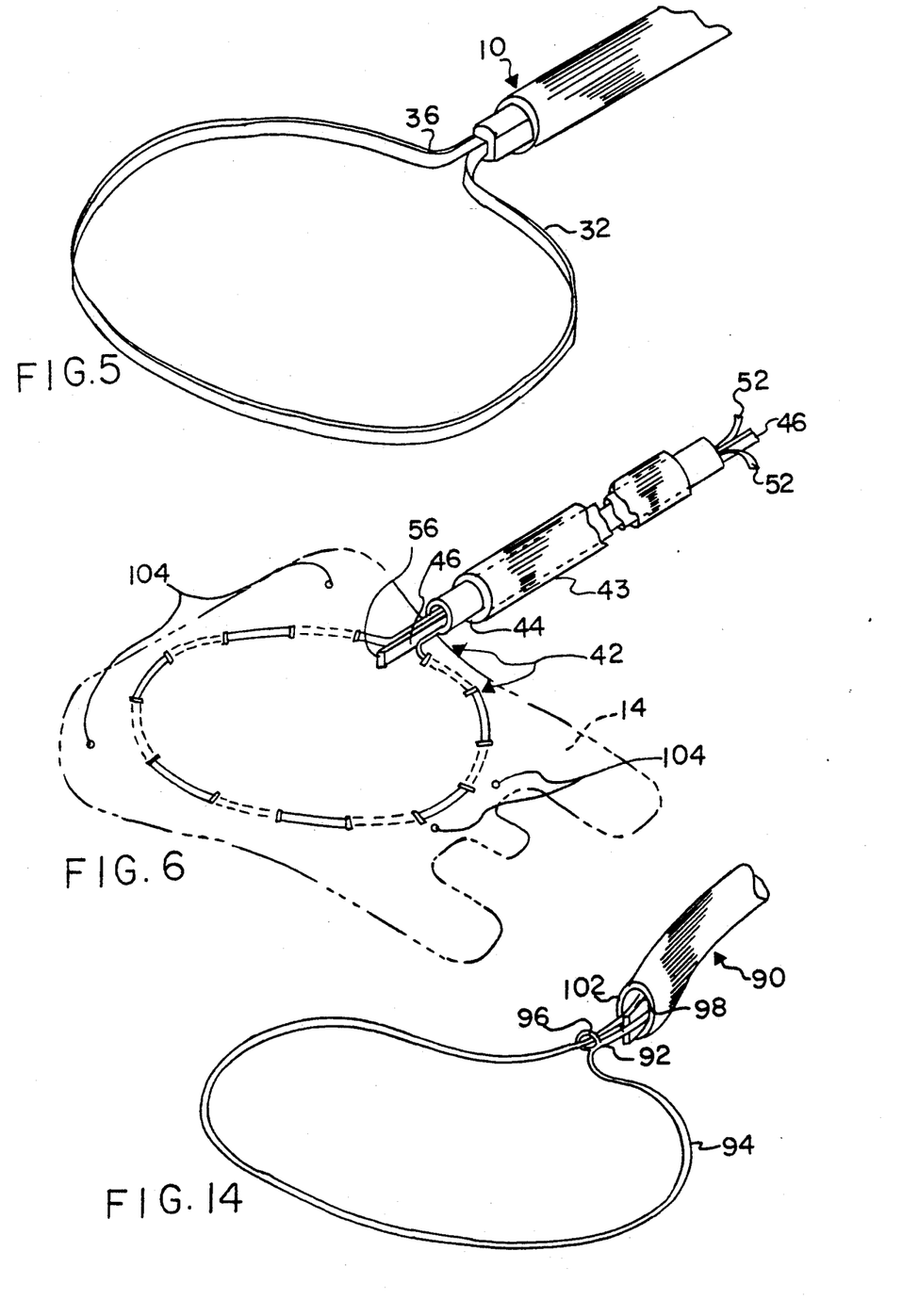
FIG. 5 is a perspective illustration of a portion of the introducer including an exterior sheath and plunger/expander assembly.
FIG. 6 is a perspective illustration of the patch of FIG. 4 with the patch introducer of FIG. 5 and with parts broken away to show certain internal constructions thereof.
FIG. 14 is a perspective illustration of a patch delivery assembly constructed in accordance with a further alternate embodiment of the invention.

In yet a further embodiment of the introducer 90, that shown in FIG. 14, the ribbon 92 is replaced by a looped mono-filament thread. The mono-filament thread is preferably of a surgically antiseptic, durable, inextensible material. By way of example, acceptable materials are Nylon, polypropylene and polyglycolic acid including PDS. PDS is a tradename of the Johnson and Johnson Company of Sommerville, N.J. These typically materials will allow the threads to be pushed from the introducer by the surgeon. The thread is shaped with a loop 94 received at its distal end. The proximal ends of the thread are for pushing and pulling the thread, and consequently blooming the patch, with respect to the plunger and sheath.

An intermediate portion of the thread is formed with an eyelet 96 adjacent to the proximal end of the plunger for the sliding passage of the proximal end of the thread. As in the embodiment discussed immediately, hereinabove, the loop supporting the patch is formed as a lasso. The two proximal ends of the thread are manipulated by a surgeon during operation and use. A guide beam 98 shaped as an I-beam is incorporated within the plunger to guide the movement of the thread ends with respect to the plunger during the blooming of the patch. There is no need for a direct attachment of the loop to the plunger as this occurs passively. There is, however, a need for coupling the patch to the eyelet for proper patch placement. With the thread and patch dispensed outside the sheath as described above, the proximal end of the thread end passing through the eyelet is pushed so that a central extend of the thread begins to move forward out of the sheath to effect the blooming of the patch.

In all of the embodiments requiring thread removal, after final positioning of the patch, the proximal end of the patch must be cut from its attachment from the introducer, block or eyelet ribbon while the distal end of the loop must be cut so that the introducer and ribbon may be withdrawn from the patch and site of the operation.

In the embodiment of FIGS. 4 and 11 through 13, when the loop is formed of an absorbable material, the loop must be cut free of the remainder of the ribbon.

It should be understood that a wide variety of mechanisms could be used to support the patch and to effect its blooming and positioning. In the disclosed embodiments herein, the mono-filament thread could be replaced by a ribbon and the ribbon could be replaced by a mono-filament thread. Further, a wide variety of materials could be substituted between the thread embodiment and ribbon embodiments including the use of absorbable, biodegradable or biocompatible materials for the loop that need not be removed. One typical material is a copolymer of glycolide and lactide of the type marketed under the tradename Vicril by Ethicon, a division of Johnson & Johnson of Sommerville, N.J.

Note is taken that the FIG. 14 embodiment illustrates the introducer 90 with a slight curve. This slight curve allows the surgeon to more readily axially rotate the introducer and thus the patch, for a more precise patch positioning. Such curve may also be utilized in the plug introducer assembly discussed hereinafter. The introducer may be of a slightly flexible nature. Conventional straight or flexible sleeves may, of course, also be employed.

One distinguishing characteristic of the present invention is the shaping of the distal end of the introducer with a bevel 102. This will allow the surgeon to view the orientation of the introducer and patch on a monitor or through an operating laparoscope prior to moving the patch from the interior of the introducer. In addition, radiopaque markers 104 on the patch and/or plug could be utilized for determining their orientation and location by conventional radiographic techniques.

Plug and Introducer

Plugs are shown in FIGS. 15 and 16 while their introducer 110 is shown in FIGS. 17 through 19. The FIG. 15 plug 12 is simply a piece of surgical fabric or mesh such as Marlex ® mesh. The material is spirally wrapped to form a mending component in a generally cylindrical shape. The term generally cylindrical shape is intended to include components which have a taper, as for example a truncated cone. It may also be fabricated as a one piece molded object of an open cell foam of a sponge like nature.

The FIG. 16 plug 112 is similar in construction to the FIG. 15 plug 12. It includes, in addition, a flange 114. The flange is preferably fabricated of a material similar to the patch. The flange may be with or without one peripheral edge that includes a radial extension with two symmetric fingers 118 and 120 and a recess 122 for receiving an adjacent vas deferens or femoral blood vessels. The central plug component may be of an absorbable or biodegradable material to be assimilated into bodily tissue over time. The plug is also preferably formed with openings or interstices to accelerate the healing of the opening being patched through the promoting of scar tissue in growth. The plug may be made of a material such that is expands and swells if exposed to fluids. A sponge is typical of such a material.

The plug assembly 110 is seen in FIGS. 17, 18 and 19. During operation and use, the assembly is positioned through a sleeve. The assembly includes an exterior cylindrical sheath 128 and an interior cylindrical plunger 126. As seen in FIG. 17, the plug is initially located in the distal end of the sheath with the flange, if utilized, at the proximal end of the plug. The plunger is proximally located with respect to the plug.

In operation and use, the distal end of the introducer and plug is simply inserted into the hernia defect 132 and dispensed by depressing the plunger while withdrawing the sheath thereby leaving the plug in place. Additional plugs may be placed to fill the defect if excessively large. Alternatively the plug with flange may be inserted to plug the defect and support the adjacent weak tissue. The dispensing of the plug may be effected by any relative movement between the plunger and sheath, by moving the plunger with respect to the sheath or the sheath with respect to the plunger. FIG. 18 illustrates the plug in the tissue opening after being dispensed. FIG. 19 illustrates the plug without a flange. Handles at the proximal ends of the sheath and plunger assist the surgeon in this procedure. Once placed within the tissue to be repaired, the plug or plugs may be caused to swell to a large diameter through being irrigated either naturally through bodily fluids or artificially as through a saline solution introduced by the surgeon.

Methods

The plug, plug/flange assembly, and patch and their delivery apparatus may be utilized independently of each other or sequentially in system configuration, depending on the condition of the patient and the parts of the body to be repaired. The utilized mending component, whether plug or plug with flange or patch, are at the discretion of the surgeon.

During an operation, the operating laparoscope, sleeve with its contents, is positioned within the incision into the preperitoneal space. The space is dissected with insufflation of carbon dioxide or other conventional gas technique. The laparoscope and its contents are manipulated inwardly and outwardly thereof for effecting the appropriate procedures. After dissection of the space, other punctures in the abdomen are made for placement of a second or third sleeve. These additional sleeves allow for use of additional instruments for manipulation, dissection, and use of a laser or cautery. Similarly, the patch and/or plug introducers and contents are manipulated inwardly and outwardly of the sleeves.

To position the plug in its orientation adjacent to the intended area, the plug is positioned within the distal end of the introducer. The plug is initially packaged within the introducer. The introducer and its contents are advanced to within the hernial defect which is to receive the plug. The surgeon holds the proximal end of the plunger forward while the sheath is withdrawn. The plug will then move outside of the sheath into the position of FIG. 18. The plunger holds the plug against movement while allowing complete release from the sheath. Additional plugs may be inserted as needed.

To position the patch in its orientation adjacent to the intended area, the patch is positioned on the loop and located within the distal end of the introducer. The introducer and its contents are advanced to a position adjacent to the area of the abdominal wall which is to receive the patch. The patch is dispensed by the surgeon pushing the proximal end of the plunger distally while moving the sheath proximally. The patch will then move outside of the introducer with the loop resiling to the elliptical shape of FIGS. 1 and 2. The blooming of the patch is effected by the extending of the loop within the patch thus distending the patch to a proper, anatomically correct shape. This procedure may be observed by the surgeon through conventional laparoscopic techniques.

With the central portion of the patch properly positioned, the surgeon may manipulate the edges of the patch exterior of the loop, and secure the patch in proper position. Staples or sutures could be utilized but the contents of the abdominal cavity may be sufficient to apply adequate pressure to hold the patches in proper position.

With the patch having been secured around its periphery as shown in FIG. 1, the ribbon may be removed from the patch prior to the withdrawal of the introducer. Once again, conventional laparoscopic techniques may be employed to cut the ribbon at its distal end so that the ribbon may be slid from the passageway and withdrawn prior to removal of the introducer. This step is eliminated if the loop is of a degradable material. The patch and loop must then be cut away from the plunger prior to removal of the introducer.

The present invention may be utilized by a surgeon in carrying out a new laparoscopic procedure for repairing hernias.

Alternate Plug/Flange Assemblies

Shown in FIGS. 20-24 are alternate embodiments of the present invention. In accordance with the alternate embodiments, the plugs are constructed as discussed previously in the prior embodiment of FIG. 16. A flange coupled to each plug is also included as discussed previously to constitute plug/flange assemblies. In the prior embodiment, however, it is up to the surgeon to position the flange over the area of hernial weakness through tweezers in a laparoscopic procedure.

Figure 20:
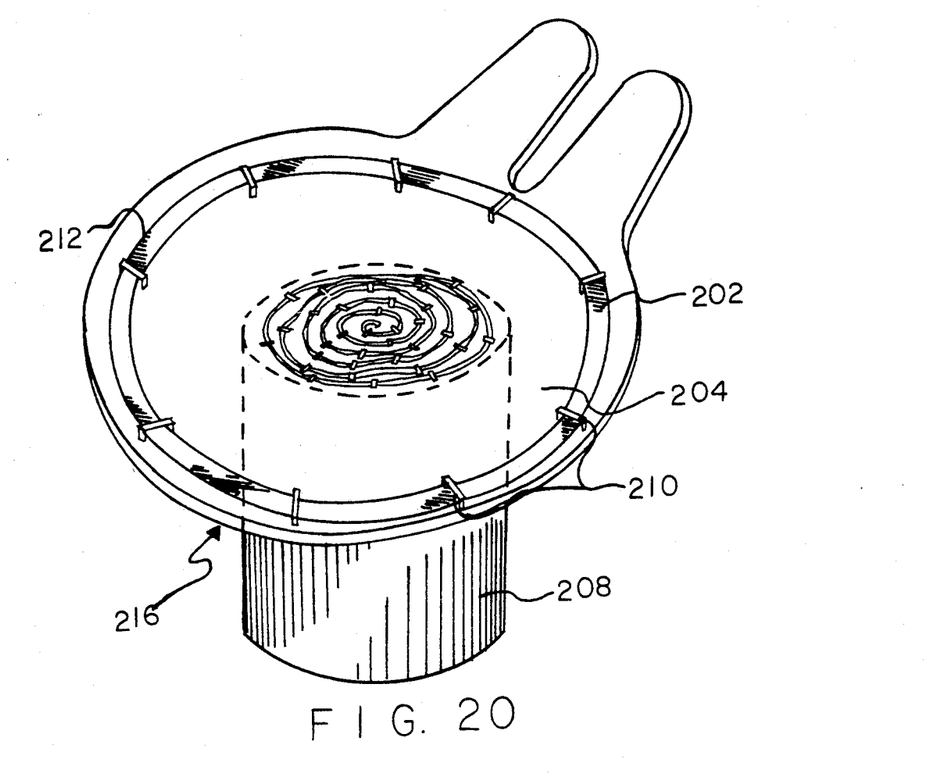
FIG. 20 is a perspective illustration of an alternate plug/flange assembly.
Figure 21:
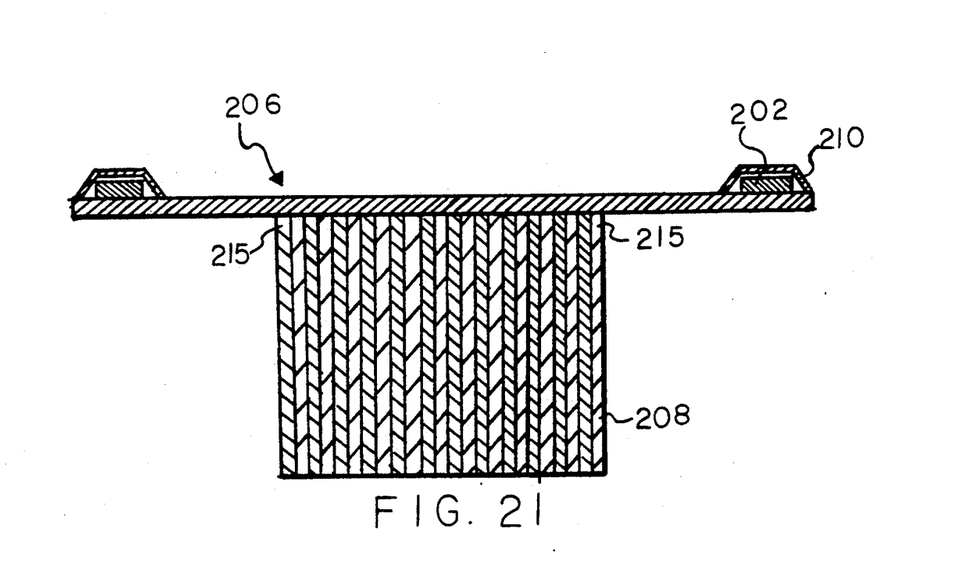
FIG. 21 is a sectional view of the assembly shown in FIG. 20 taken along line 21—21 of FIG. 20.

According to the alternate embodiment of FIGS. 20 and 21, a washer-shaped member 202, generally with a rectangular-cross-sectional configuration, of a resilient, elastomeric material, is coupled to the flange 204 in a circle adjacent to the periphery of the flange. In this manner, the washer-like member functions to return the flange 204 to the orientation as shown in FIG. 20 after being stored in a constricted configuration within a sleeve prior to utilization. The time and effort expended by a surgeon for positioning of the flange 204 is, consequently, eliminated. While stored in the sleeve, the flange 204 and its resilient member 202 are withdrawn to a constricted configuration prior to being ejected from the sleeve and placed in the body part to be repaired. In the FIG. 20 showing, the central portion of the flange is removed to show the internal construction of the plug.

The terminology plug, flange and patch are used for illustration purposes. When patching material is coupled to a plug it is called a flange but its function is to augment or restore structural integrity of the weakened abdominal wall just as the patch alone.

Prior to placement of the plug/flange assembly or device 206, the entire plug/flange assembly with its plug 208 and washer-like member 202 are located within the sleeve for being dispensed as previously discussed. As a result, dispensing of the assembly from the sleeve and locating the plug in the hernial opening will automatically position the flange in a proper orientation. A mark on the sleeve, detectable by laparoscopic observation as discussed hereinabove, is positioned on the sleeve and correlated to a predetermined portion of the flange, preferably the enlarged portion. This precludes the need for rotational orientation of the flange and ensures the proper level of insertion of the plug. If re-orientation of the plug is needed to reposition the flange, such re-orientation would have to be done laparoscopically as through tweezers, but the flange blossoming is still eliminated.

In this FIG. 20 embodiment, the washer like element has a rectangular cross sectional configuration with a radial dimension of between about 0.15 and 0.25 centimeters and an axial dimension of between about 0.05 and 0.10 centimeters. The entire washer-like element has an exterior diameter of between about 4.0 and 6.0 centimeters for allowing positioning in the sleeve when in a constricted configuration. The exterior diameter is substantially equal to the diameter of the majority of the flange.

Coupling of the washer-like element to the flange may be done through stitching 210. In the alternative, it may be woven in and out of threads of the flange. Such weaving embodiment requires that the washer-like element be provided with a radial cut 212 so that the weaving may be effected. After weaving and before use, however, the cut is preferably sealed as by welding. It may also be coupled by adhesive or glue. Stitching 211 around the periphery of the plug couples the plug to the flange. In the alternative, an appropriate adhesive could be utilized.

Figure 22:
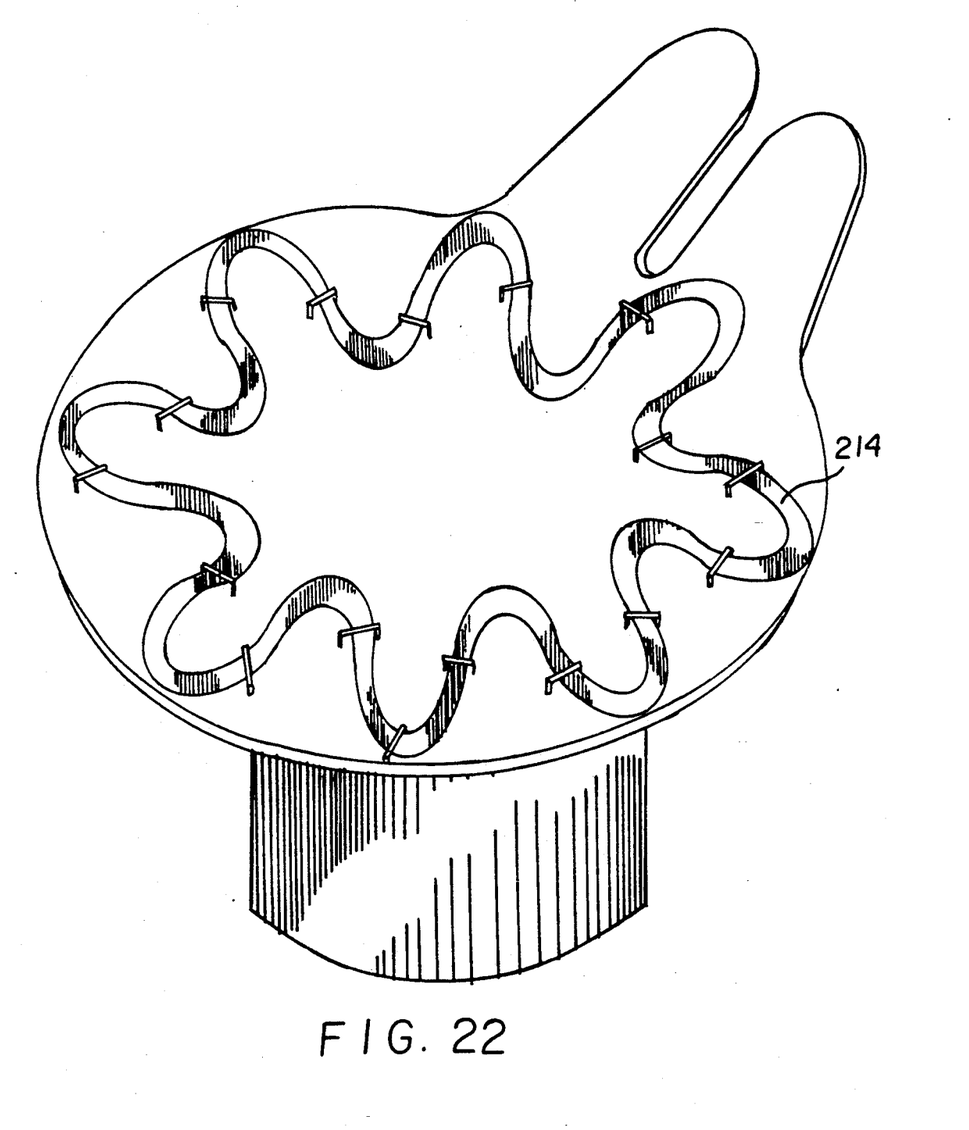
FIG. 22 is a perspective illustration of a modified resilient member for use with the assembly of FIG. 20.

A further modification of the FIG. 20 embodiment involves the shaping of a resilient element 214 in a serpentine configuration. Stitching of such serpentine resilient element 214 is the same as in the FIG. 20 embodiment and the desired resilience and positioning is accomplished properly. By construction the washer-like element 214 in the serpentine manner rather than circular as like member 202 allows the more even distribution of volume within the sleeve prior to operation and use. In other words, the volume of the washer-like element is spread more evenly along the length of the plunger and sleeve at the distal ends thereof.

Figure 23:
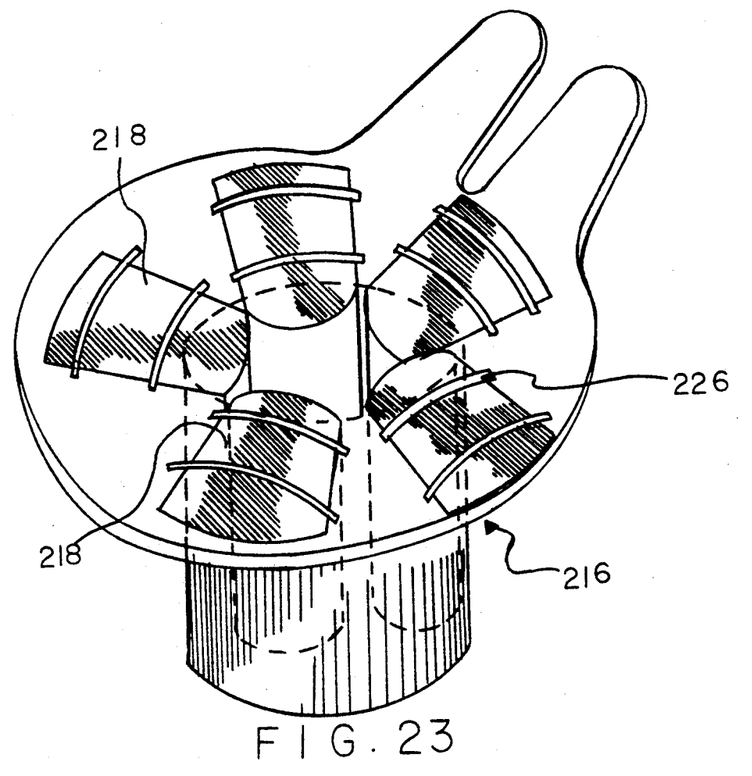
FIG. 23 is a perspective illustration of an additional alternate plug/flange assembly.
Figure 24:
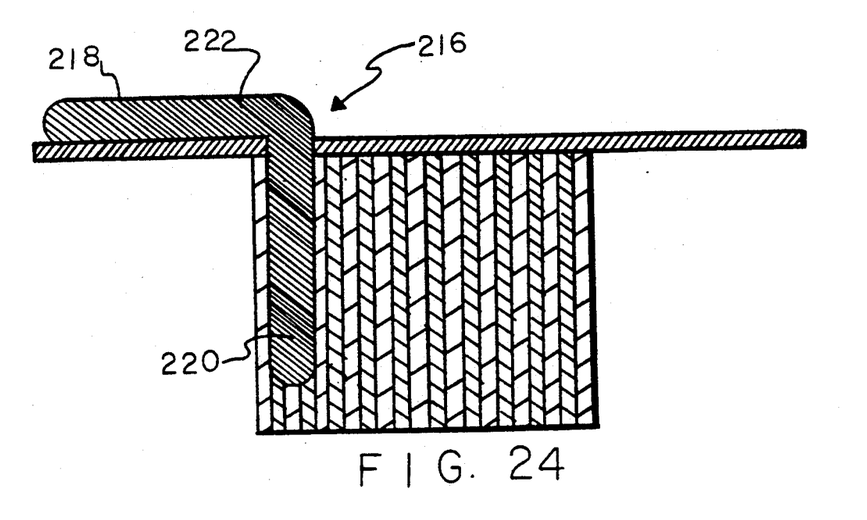
FIG. 24 is a sectional view of the assembly shown in FIG. 23 taken along line 24-24 of FIG. 23.

FIGS. 23 and 24 illustrate yet a further alternate embodiment of the plug/flange assembly 216. In this embodiment, the washer-like element is replaced with a plurality of resilient L-shaped members 218. One leg 220 of each L-shaped member is located within an exterior layer of the plug 208 wrapping material, parallel with the axis of the plug. The other leg 222 of each L-shaped member 218 extends radially outwardly from the plug to a distance just short of the external periphery of the flange 204. Five such L-shaped members are shown in the FIG. 22 illustration of this embodiment, fanning outwardly in a symmetric starburst configuration. A lesser number could be utilized so long as it continues to function in spreading out the flange in its intended generally planar configuration. A greater number could also be utilized so long as it continues to function in spreading out the flange and can be fit within the sleeve during storage and prior to use. The legs 220 and 222 of the L-shaped members 218 are coupled to the flange material through stitching 226 as shown, or they may be woven through the fabric at spaced apart points. The individual L-shaped members 218 are formed of a resilient material, metal, plastic, or other biocompatible material to assume the natural configuration with a right angle bend therein, as shown. They are also adapted to be bent into a linear or essentially linear orientation when stored within the sleeve with the plug/flange assembly prior to use. Each L-shaped member has legs which are between about 1.5 and 4.0 centimeters in length, between about 0.2 and 0.5 centimeters in width and between about 0.10 and 0.20 centimeters in thickness with the bend located to coincide with the junction of plug and flange, generally at about the midpoint. The sizes are variable as a function of the size of the channel, the thickness of the patch material, the plug size, extent of the hernial weakness, hernial opening, etc.

Prior to placement of the plug/flange device 206, the entire plug/flange device with its plug 208 and L-shaped members 202 are located within the sleeve for being dispensed as previously discussed. As a result, dispensing of the assembly from the sleeve and locating the plug in the hernial opening will automatically position the flange in a proper orientation.

The flange and plug are, as in the prior embodiments, preferably fabricated of a material which is not absorbable by the patient's body through the passage of time. The resilient material may, however, be biodegradable by the patient's body since its function is completed upon the proper positioning of the flange during the surgery.

Figure 25:
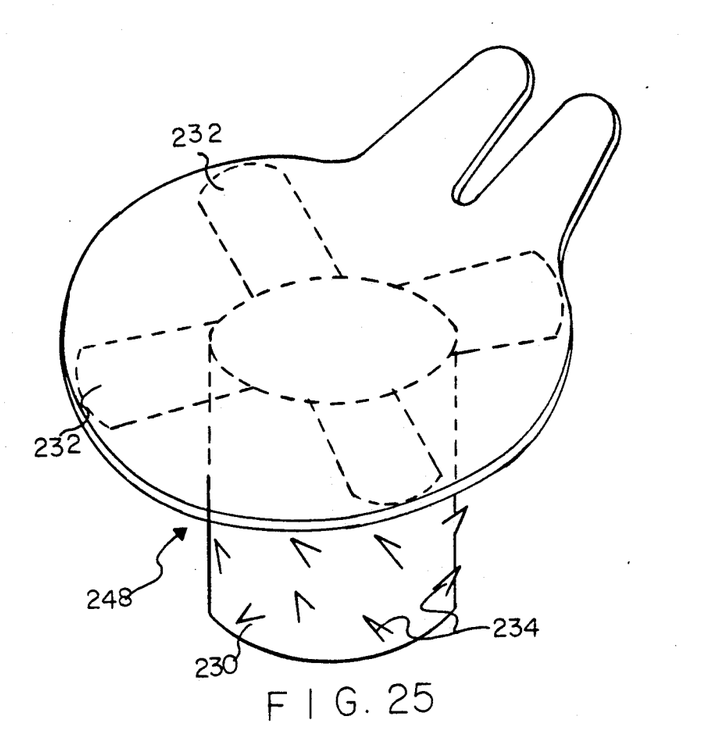
FIG. 25 is a perspective illustration of an additional alternate plug/flange assembly.
Figure 26:
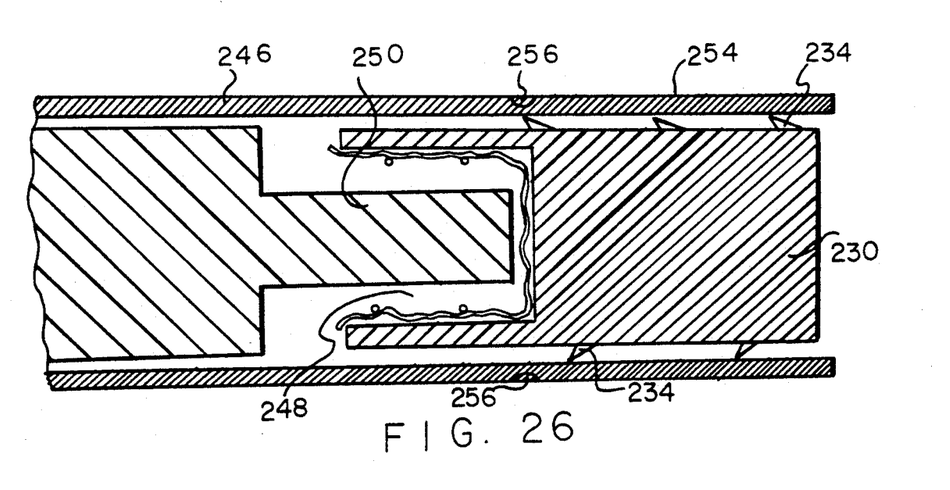
FIG. 26 is a plan view of a modified plunger for accommodating the alternate plug/flange assemblies of FIGS. 20-24 with parts removed to show internal constructions.

The FIG. 25 embodiment illustrates a plug 230 fabricated of a one piece molded construction. Such plug/flange assembly is also seen in cross sectional view in FIG. 26 where it is loaded in a sheath for being dispensed. Extending proximally from the plug are the resilient members 232 formed integrally with the plug for functioning as in the prior embodiments of the plug/flange assemblies. FIG. 26 shows the resilient members prior to being dispensed. FIG. 25 shows the resilient members after moving to their natural orientation. In this embodiment, the exterior surface of the plug 230 is roughened to increase its frictional contact with the tissues and maintain its position within the patient. In the alternative, needle-like projections 234 may be molded into the exterior surface of the plug as shown in FIGS. 25 and 26. This also increases the frictional contact between the plug and the tissues. The projections preferably extend generally radially from the plug and are angled proximally thereof.

An alternate plunger is shown in FIG. 26. The plunger is located within a sleeve as in the prior embodiments with the plug/flange assembly at the distal end thereof. In order to accomodate the added volume of the flange generated by either washers 202 or 214 or the L-shaped members 218, the distal end of the plunger 244 is of a reduced diameter to generate a space 248 therearound and within the sleeve 246 for accomodating the volume of the flange and its resilient member or members. In this manner, the distal end 250 of the plunger may contact the proximal end of the plug for inserting the plug in the appropriate hernial opening.

As referred to hereinabove, markings are preferably formed on the sleeve to indicate the linear and rotational orientation of the sleeve and, hence, the flange. To that extent an axial marking 254 on the sleeve 246 extends proximally from the distal ed to a location for indicating the proximal end of the plug and the enlarged portion of the flange. A circumferential marking 256 extends around the sleeve 246 to indicate the proximal end of the plug. Either one or both or alternate markings could be utilized for these purposes. Such markings could be visually observable or of a radiopaque material as is well known in the arts.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:

1. Apparatus for the repair of hernias comprising a cylindrical, non tubular plug positionable in an opening in the abdominal wall to be repaired with the plug in contact with the opening, the plug having a distal end and a proximal end; a patch of a flexible essentially inextensible material positionable over portions of the abdominal wall adjacent to the opening, a central extent of the patch being coupled to the proximal end of the plug with the periphery of the patch remote from the plug constituting a flange; and resilient means of a biocompatible material coupled to the flange and provided with memory to assume a configuration of an extended shape for the proper positioning of the flange with respect to the portions of the abdominal wall, the length of the plug being several times greater than the thickness of the patch and resilient means.

2. The apparatus as set forth in claim 1 wherein the resilient means is a washer-shaped member secured to the flange adjacent to its periphery.

3. The apparatus as set forth in claim 2 wherein the washer-shaped member is between about 4.0 and 6.0 centimeters in its exterior diameter.

4. The apparatus as set forth in claim 2 wherein the washer-shaped member is deformable to a configuration for positioning within a sleeve.

5. The apparatus as set forth in claim 1 wherein the resilient means is a serpentine-shaped member secured to the flange along a periphery of said flange.

6. The apparatus as set forth in claim 1 wherein the resilient means is a plurality of L-shaped components, each component having one leg positioned within the plug and parallel to the axis of the plug and having another leg coupled with respect to the flange and extending radially from the axis of the plug.

7. The apparatus as set forth in claim 6 wherein the plurality of L-shaped components are bendable to an essentially linear configuration for positioning within a sleeve.

8. The apparatus as set forth in claim 1 wherein the plug is fabricated of fabric rolled spirally into a cylindrical configuration.

9. The apparatus as set forth in claim 1 wherein the plug is of a one piece construction.

10. The apparatus as set forth in claim 9 wherein the exterior surface of the plug is roughened to increase its coefficient of friction.

11. The apparatus as set forth in claim 9 wherein the exterior surface of the plug includes frictional members extending radially from the exterior surface of the plug.

12. The apparatus as set forth in claim 1 and further including a sheath for the receipt of the plug/flange assembly, the sheath being flexible.

13. A laparoscopic systems comprising:
a plug/patch assembly comprising a cylindrical plug of a flexible material positionable in an opening in the abdominal wall to be repaired with the plug in contact with the opening, the plug having a distal end and a proximal end; a patch of an inextensible, flexible mesh material positionable over weakened portions of the abdominal wall adjacent to the opening, a central extent of the patch being coupled to the proximal end of the plug with the periphery of the patch remote from the plug and constituting a flange; and resilient means coupled to the flange and provided with memory to assume a configuration of an extended shape for the proper positioning of the flange with respect to the weakened portions of the abdominal part;
a cylindrical sleeve of the length to extend from exterior of a patient, through a laparoscopic opening into a surgical cavity; and
a plunger having a cylindrical exterior configuration positioned with the sleeve, the plunger having a distal end of a reduced radial size to form a space at the distal end of the sleeve for the receipt of patch material of said plug/patch assembly.

* * * * *